US010506960B2

United States Patent
Kaestle (10) Patent No.: US 10,506,960 B2
(45) Date of Patent: Dec. 17, 2019

(54) SYSTEM FOR SCREENING OF THE STATE OF OXYGENATION OF A SUBJECT

(71) Applicant: KONINKLIJKE PHILIPS N.V., Eindhoven (NL)

(72) Inventor: Siegfried Walter Kaestle, Nuffringen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 849 days.

(21) Appl. No.: 14/902,866

(22) PCT Filed: Jun. 30, 2014

(86) PCT No.: PCT/EP2014/063787
§ 371 (c)(1),
(2) Date: Jan. 5, 2016

(87) PCT Pub. No.: WO2015/003938
PCT Pub. Date: Jan. 15, 2015

(65) Prior Publication Data
US 2017/0319114 A1    Nov. 9, 2017

Related U.S. Application Data

(60) Provisional application No. 61/844,460, filed on Jul. 10, 2013.

(30) Foreign Application Priority Data

Jul. 10, 2013   (EP) ..................................... 13175927

(51) Int. Cl.
*A61B 5/1455*    (2006.01)
*A61B 5/00*      (2006.01)
(Continued)

(52) U.S. Cl.
CPC ........ *A61B 5/14551* (2013.01); *A61B 5/0077* (2013.01); *A61B 5/02416* (2013.01);
(Continued)

(58) Field of Classification Search
None
See application file for complete search history.

(56) References Cited

U.S. PATENT DOCUMENTS 6,415,166 B1    7/2002   Van Hoy
6,775,565 B1    8/2004   Wieringa
(Continued)

FOREIGN PATENT DOCUMENTS

DE    102010056615    7/2012
EP    2319398         5/2011
(Continued)

OTHER PUBLICATIONS

Toth, "Oxygen saturation in healthy newborn infants immediately after birth measured by pulse oximetry", Archives of Gynecology and Obstetrics, Springer Verlag, Berlin, DE, vol. 266, No. 2, Apr. 1, 2002, pp. 105-107.

(Continued)

*Primary Examiner* — Eric F Winakur
*Assistant Examiner* — Marjan Fardanesh (57) ABSTRACT

The present invention relates to a processor and a system (1, 1') for screening of the state of oxygenation of a subject (100), in particular for screening of newborn babies for congenital heart disease. The system comprises an imaging unit (2) for obtaining a plurality of image frames of the subject (100) over time, and a processor (3) for processing the image frames. The imaging unit, for instance a conventional video camera as used in the vital signs monitoring using the above mentioned principle of remote PPG, is used as a contact less pulse oximeter, by use of which a body map (Continued)

(for at least some body parts of interest) of at least the blood oxygen saturation is created. Picking certain body areas, e.g. right upper extremity versus left upper and/or lower extremity, and combining or comparing them can serve the purpose of detecting anomalies of heart and/or circuitry functions.

15 Claims, 7 Drawing Sheets

(51) Int. Cl.
*A61B 5/024* (2006.01)
*A61B 5/08* (2006.01)

(52) U.S. Cl.
CPC ........ *A61B 5/14557* (2013.01); *A61B 5/7275* (2013.01); *A61B 5/7278* (2013.01); *A61B 5/0816* (2013.01); *A61B 5/6825* (2013.01); *A61B 5/6829* (2013.01); *A61B 2503/045* (2013.01); *A61B 2576/00* (2013.01); *A61B 2576/023* (2013.01)

(56) References Cited

U.S. PATENT DOCUMENTS

| 6,909,912 | B2 | 6/2005 | Melker |
| 2008/0045818 | A1 | 2/2008 | Wood |
| 2008/0071155 | A1 | 3/2008 | Kiani |
| 2009/0281839 | A1 | 11/2009 | Lawrence |
| 2010/0224191 | A1 | 9/2010 | Dixon |
| 2011/0031114 | A1 | 2/2011 | Park |
| 2011/0231205 | A1 | 9/2011 | Letts |
| 2012/0330109 | A1 | 12/2012 | Bao |

FOREIGN PATENT DOCUMENTS

| WO | 2008094253 | 8/2008 |
| WO | 2013/017976 | 2/2013 |
| WO | 2013027027 | 2/2013 |

OTHER PUBLICATIONS

Humphreys, "A CMOS Camera-Based Pulse Oximetry Imaging System" Engineering in Medicine and Biology Society, 2005. IEEE-EMBS 2005. 27th Annual International Conference of the, Date of Conference: Jan. 17-18, 2006, pp. 3494-3497.
Humphreys, "Noncontact simultaneous dual wavelength photoplethysmography: A further step toward noncontact pulse oximetry", Review of Scientific Instruments 78, 044304, 2007.
Mahle, "Role of Pulse Oximetry in Examining Newborns for Congenital Heart Disease". Circulation 2009;120;447-458.
Ewer, "Pulse oximetry screening for congenital heart defects in newborn infants (PulseOx): a test accuracy study". Lancet 2011; 378: 785-94.
Wieringa, "In Vitro Demonstration of an SpO2-Camera", Computers in Cardiology 2007;34:749-751.
Hoke, et al: Oxygen Saturation as a Screening Test for Critical Congenital Heart Disease. Pediatr Cardiol 23:403-409, 2002.
Zaramella et al., "Foot Pulse Oximeter Perfusion Index Correlates with Calf Muscle Perfusion Measured by Near-Infrared Spectroscopy in Healthy Neonates", Journal of Perinatology, (2005), 25, pp. 417-422.

SYSTEM FOR SCREENING OF THE STATE OF OXYGENATION OF A SUBJECT

CROSS REFERENCE TO RELATED APPLICATIONS

This application is a national filing of PCT application Serial No. PCT/EP2014/063787, filed Jun. 30, 2014, published as WO 2015/003938 on Jan. 15, 2015, which claims the benefit of U.S. Provisional Application No. 61/844,460 filed Jul. 10, 2013 and European Patent Application Number 13175927.6 filed Jul. 10, 2013, all of which are incorporated herein by reference.

FIELD OF THE INVENTION

The present invention relates to a system for screening of the state of oxygenation of a subject, in particular of an infant or newborn baby. Further, the present invention relates to a processor and a processing method for processing image frames obtained from a subject over time. The present invention relates particularly to the screening of newborn babies for critical congenital heart disease (CCHD) in a contactless manner.

BACKGROUND OF THE INVENTION

Vital signs of a person, for example the heart rate (HR), the respiration rate (RR) or the blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heart beat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmissivity and/or reflectivity at different wavelengths (typically red and infrared), the blood oxygen saturation can be determined.

Conventional pulse oximeters for measuring the heart rate and the oxygen saturation of a subject are attached to the skin of the subject, for instance to a finger tip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmissivity of the same area or volume of tissue at two different wavelengths. This is referred to as time-division-multiplexing. The transmissivity over time at each wavelength gives the PPG waveforms (also called PPG signals) for red and infrared wavelengths. Although contact PPG is regarded as a basically non-invasive technique, contact PPG measurement is often experienced as being unpleasant, since the pulse oximeter is directly attached to the subject and any cables limit the freedom to move.

Recently, non-contact, remote PPG devices for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications.

Wieringa, et al., "Contactless Multiple Wavelength Photoplethysmographic Imaging: A First Step Toward "SpO2 Camera" Technology," Ann. Biomed. Eng. 33, 1034-1041 (2005), discloses a remote PPG system for contactless imaging of arterial blood oxygen saturation in tissue based upon the measurement of plethysmographic signals at different wavelengths. The system comprises a monochrome CMOS-camera and a light source with LEDs of three different wavelengths. The camera sequentially acquires three movies of the subject. During each movie, the subject is illuminated by the light source at a different wavelength. The pulse rate can be determined from a movie at a single wavelength, whereas at least two movies at different wavelengths are required for determining the oxygen saturation. The measurements are performed in a darkroom, using only one wavelength at a time. The patient is not allowed to move between the subsequent measurements at different wavelengths. A further problem is that a measurement in darkness is not practical for unobtrusive medical and non-medical applications.

Toth B. et al.: "Oxygen saturation in healthy newborn infants immediately after birth measured by pulse oximetry", Archives of Gynecology and Obstetrics, Springer Verlag, Berlin, DE, Vol. 266, No. 2, 1 Apr. 2002, pages 105-107 discloses a study of the measurement of pre- and postductal arterial oxygen saturation rates that were measured in 50 healthy newborn infants. Two pulse oximeters were used to measure $SpO_2$ continuously with sensors placed around the ulna side of the right wrist and around the right midfoot, representing pre- and postductal $SpO_2$ value respectively. It was found that neonates need approximately 15 min to reach adult $SpO_2$ values.

DE 10 2010 056 615 A1 discloses a camera-based transillumination measurement device for contactless space-resolved vital parameter determination of neonates from camera images.

US 2011/0311143 A1 discloses a method of controlling a function of a device and system for detecting the presence of a living being.

WO 2013/017976 A1 discloses a device for obtaining an processing measurement readings including at least a component representative of a physical phenomenon in a living being, comprising a sensor for obtaining measurement readings from at least one body part of a living being from a distance having at least a component representative of the physical phenomenon in the living being, an identification unit for identifying the at least one body part of the living being; an extraction unit for extracting at least one first signal from the measurement readings representing at least one component representative of the physical phenomenon, an evaluation unit for obtaining adjustment information according to the at least one identified body part, and an adjustment unit for adjusting the at least one first signal according to the adjustment information and for generating at least one output signal representing the physical phenomenon of the living being.

SUMMARY OF THE INVENTION

It is an object of the present invention to provide an improved system, processor and method enabling the screening of the state of oxygenation of a subject, in particular of an infant or newborn baby for critical congenital heart disease, in a contactless manner, which may e.g. be used for generally screening all newborn babies.

In a first aspect of the present invention a processor for use in a system for screening of the state of oxygenation of a subject, said system comprising an imaging unit for obtaining a plurality of image frames of the subject over time, said processor being configured to process the image frames by recognizing the subject within an image frame,
locating body parts of interest of the subject including at least the right upper extremity and at least one lower extremity of the subject,
determining, per body part of interest, the perfusion index,
selecting, per body part of interest, a plurality of pixels and/or pixel groups by use of said perfusion index,
determining the blood oxygen saturation level for said plurality of pixels and/or pixel groups of the subject from pulse oximetry waveforms for at least two different wavelengths contained in the image frames,
determining a difference blood oxygen saturation level between the determined blood oxygen saturation level for the right upper extremity and the determined blood oxygen saturation level for the at least one lower extremity, and
comparing the determined difference blood oxygen saturation level, the determined blood oxygen saturation level for the right upper extremity and the determined blood oxygen saturation level for the at least one lower extremity to respective blood oxygen saturation level thresholds to obtain a screening indicator for the subject indicating the quality of the subject's oxygenation.

In a further aspect of the present invention a system for screening of the state of oxygenation of a subject is presented, said system comprising an imaging unit for obtaining a plurality of image frames of the subject over time, and a processor as proposed herein for processing the image frames.

In a further aspect of the present invention a processing method for processing image frames obtained from a subject over time is provided.

In yet another aspect of the present invention, there is provided a computer program which comprises program code means for causing a computer to perform the steps of the proposed processing method when said computer program is carried out on a computer. Further, a non-transitory computer-readable storage medium that stores therein such a computer program product, which, when executed by a processor, causes said steps of the processing method disclosed herein to be performed, is presented.

Preferred embodiments of the invention are defined in the dependent claims. It shall be understood that the claimed processor, processing method, computer program and medium have similar and/or identical preferred embodiments as the claimed system and as defined in the dependent claims.

The present invention is based on the idea to use an imaging unit, for instance a conventional video camera as used in the vital signs monitoring using the above mentioned principle of remote PPG, as a contactless pulse oximeter, by use of which a body map (for at least some body parts of interest) of at least the blood oxygen saturation (sometimes also referred to as SpO2, meaning the blood oxygen saturation measured by pulse oximetry, quasi-arterial) is created. Picking certain body areas, e.g. right upper extremity versus left upper and/or lower extremity, and combining or comparing them can serve the purpose of detecting anomalies of heart and/or circuitry functions.

The standard method used in neonatal intensive care units (NICUs) today and being established now more and more for screening of all newborn babies compares right arm/hand (pre-duct) to left arm/hand or any leg (post-duct) using two regular pulse oximeters or just one pulse oximeter in sequence. This method may be generalized according to embodiments of the present invention with the imaging unit to include more pre-duct sites like the head and more post-duct sites like one or both feet/legs and the left arm/hand and core body at the same time. The perfusion index is additionally used to select only useful pixel or pixel areas for determining the respective blood oxygen saturation level. An optional combination with pulse rate and quality indicator figures allows for much more robust detection.

The proposed contactless method is extremely well-suited for the screening purpose as it avoids cross-contamination and any effort in applying sensors. Tracking of multiple sites at a time may also indicate the overall cardio-vascular stability of the subject.

As used herein, the term "wavelength" also refers to a band of wavelengths or wavelength portion. It is to be understood as a spectral range having a limited spectral width. For example, for an optical filter the term wavelength refers to a pass band of the filter. Hence, the term wavelength is not limited to one single wavelength but is also used for a wavelength range, for example of some nanometers or some tens of nanometers, around a center wavelength. Moreover the term wavelength in the context of a filter can also refer to multiple discontinuous spectral ranges of one and the same filter element.

As used herein, the term "imaging unit" refers to a device for detecting electromagnetic radiation. In a preferred embodiment, the imaging unit is a camera with an image sensor, such as a CCD or CMOS image sensor, that comprises an array of light sensitive pixels. The output of the detection unit is referred to as radiation data. For example, the radiation data is a series of images over time, thus a video stream. The camera is preferably a color camera that is capable to create two colors of the image, typically a red and an infrared image, in a well-controlled wavelength range for accurate measurements. An RGB image sensor for a color camera comprises a color filter array with filters for the red, green and blue color channel. When using an RGB color camera, the overall filter characteristic of the system includes both the transmission characteristic of the marker areas as well as the filter characteristic of the color channels of the camera.

Further, in the context of the present invention the "right upper extremity" shall be understood as one or more of the right hand, right arm and right shoulder, or a portion of one or more of said body parts. Similarly, the "at least one lower extremity" shall be understood as one or more of the left and/or right foot, leg and limb, or a portion of one or more of said body parts.

According to an embodiment of the present invention the system further comprises a display for displaying an oxygenation image of the subject in which for selected pixels and/or pixel groups the respective blood oxygen saturation level is displayed. Preferably, the display is configured to display the oxygenation image of the subject as a false color image in which for selected pixels and/or pixel groups the respective blood oxygen saturation level is displayed in false colors. In order to present a map a good way is to use color coding. Such an image may reveal more information than just the screening indicator. For instance, if the user can see a clear gradient from right upper extremity (right shoulder/arm/hand) towards the rest of the body it gives a good confidence about a cyanotic CCHD issue. If the pattern is more random the confidence to detect a disease is lower.

Optionally, the processing unit is configured to determine, separately for the right upper extremity and at least one lower extremity (and, in further embodiments, for other body parts of interest), a combined blood oxygen saturation level from the blood oxygen saturation levels obtained for different groups of image frames, in particular for different time sequences of image frames, determine the difference blood oxygen saturation level between the determined combined blood oxygen saturation level for the right upper extremity and the determined combined blood oxygen saturation level for the at least one lower extremity, and compare the determined difference blood oxygen saturation level, the determined combined blood oxygen saturation level for the right upper extremity and the determined combined blood oxygen saturation level for the at least one lower extremity to respective blood oxygen saturation level thresholds to obtain the screening indicator for the subject.

This provides more reliable and accurate screening results. The respective blood oxygen saturation level thresholds may be predetermined and fixed. In an embodiment the thresholds may be selected depending on the type of subject to be screened (e.g. newborn baby, child, elder person, etc.). The thresholds may also be adaptable by the user, e.g. a physician or nurse carrying out the screening.

A combined blood oxygen saturation level is preferably determined from the blood oxygen saturation levels obtained for different groups of image frames by forming an average, a median, a difference or a standard deviation.

In a further embodiment, the processing unit is configured to determine, per body part of interest, the pulse rate and/or a quality index indicating the pulse oximetry signal quality and to use the determined the pulse rate and/or a quality index to qualify the obtained screening indicator. These additional parameters may be used additionally to determine the screening results to increase reliability and robustness of the screening.

In another embodiment, the processing unit is configured to use the determined perfusion index for selecting, per body part of interest, pixels and/or pixel groups, for which the previously determined blood oxygen saturation levels are binned per body part of interest, having a perfusion index above a perfusion threshold. This also contributes to improve the reliability of the screening results since areas which are (substantially) useless for pulse oximetry determinations are thus excluded. The perfusion threshold is generally predetermined, but may also be selected according to the type of subject to be screen, or may even be adaptable by the user.

A similar advantage is obtained by another embodiment according to which the processing unit is configured to use the determined perfusion index for selecting, per body part of interest, pixels and/or pixel groups, for which the pixel intensities (sometimes also referred to as pixel values) are binned per body part of interest before determining the respective blood oxygen saturation level from the binned pixel intensities, having a perfusion index above a perfusion threshold or fulfilling another selection criterion related to the perfusion index.

To provide an automatic identification of the subject so that measurements and results can be automatically assigned to the subject and his/her record, the system preferably comprises an identification unit for identifying the subject from one or more image frames, in particular by use of image recognition of an identification element, e.g. a wrist band or name tag, worn by the subject.

Motion artifact is an issue in pulse oximetry in general but especially for the camera based measurement as the body part and sensors are completely mechanically decoupled. Besides known methods of image tracking and stabilization that should be applied to the images prior to further processing, it is proposed in an embodiment of the present invention to provide holding elements for holding the subject in place while the image frames are obtained. For instance, fixation means for the limbs of interest may be provided. Screening takes a short period of time and a sort of cuff as part of a special screening bassinette could be used to hold at least the right upper extremity and another limb in place for the screening time to secure good signals and minimize motion impact. Another way to achieve little body movement is to make the bassinette's boundaries match the shape of the body and restrict arm and leg movement freedom to a large extent.

In a further embodiment the processing unit is configured to use the determined perfusion index is used to select, per body part of interest, said pixels and/or pixel groups, for which the previously determined blood oxygen saturation levels are binned per body part of interest or for which the pixel intensities are binned per body part of interest before determining the respective blood oxygen saturation level from the binned pixel intensities.

Optionally the system further comprises a light source for emission of light at said first wavelength and/or at said second wavelength in order to ensure that sufficient light at the respective wavelength is available. Further optionally, the system comprises a control unit to control the light power such that the detection unit can be operated in its optimum operating point, in particular such that for example noise or alternatively saturation effects do not disturb the measurement. In a preferred embodiment, however, the system only uses ambient light.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
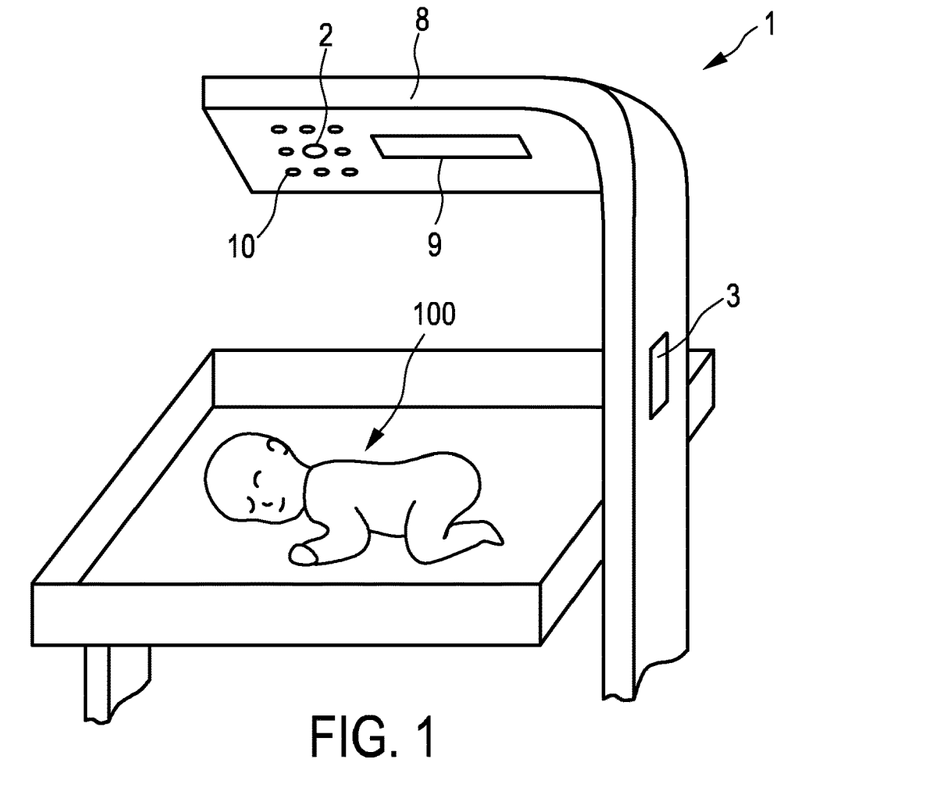
FIG. 1 shows an exemplary embodiment of the system for screening of oxygenation of a subject according to the present invention.

FIG. 1 shows an exemplary embodiment of a system 1 for screening of oxygenation of a subject 100, in this example of a newborn baby, according to the present invention. The system 1 comprises an imaging unit 2, e.g. a video camera, for obtaining a plurality of image frames of the subject 100 over time and a processing unit 3, e.g. a processor or computer, for processing the image frames. The imaging unit 2 is mounted at a predefined position to a mounting arm 8, which in this embodiment also carries the processing unit 3, e.g. at its outer surface or incorporated into the mounting arm 8.

The mounting arm 8 may e.g. be configured as radiant warmer and may thus carry additional elements like an IR warming lamp 9 centered above the baby 2. Further, it could also contain illumination elements 10 to support the camera 2 as well as other elements like display, control unit, etc. as will be explained in more detail below. Cable routing can be managed there inside the mounting arm 8, if all elements are integrated in the mounting arm 8.

Before details and further embodiments of the proposed system and method will be explained, the determination of vital sign information of a subject with the system 1 according to the present invention shall be described with reference to FIG. 2.

The term 'vital sign' as used in the context of the present invention refers to a physiological parameter of a subject and derivative parameters. In particular, the term 'vital sign' comprises heart rate (HR) (sometimes also called pulse rate), heart rate variability (pulse rate variability), pulsatility strength, perfusion, perfusion indicator, perfusion variability, Traube Hering Mayer waves, respiratory rate (RR), body temperature, blood pressure, a concentration of a substance in blood and/or tissue, such as an oxygen saturation or a glucose level.

The term 'vital sign information' as used in the context of the present invention comprises the one or more measured vital signs as defined above. Furthermore, the term 'vital sign information' comprises data referring to a physiological parameter, corresponding waveform traces or data referring to a physiological parameter over time that can serve for subsequent analysis.

Figure 2:
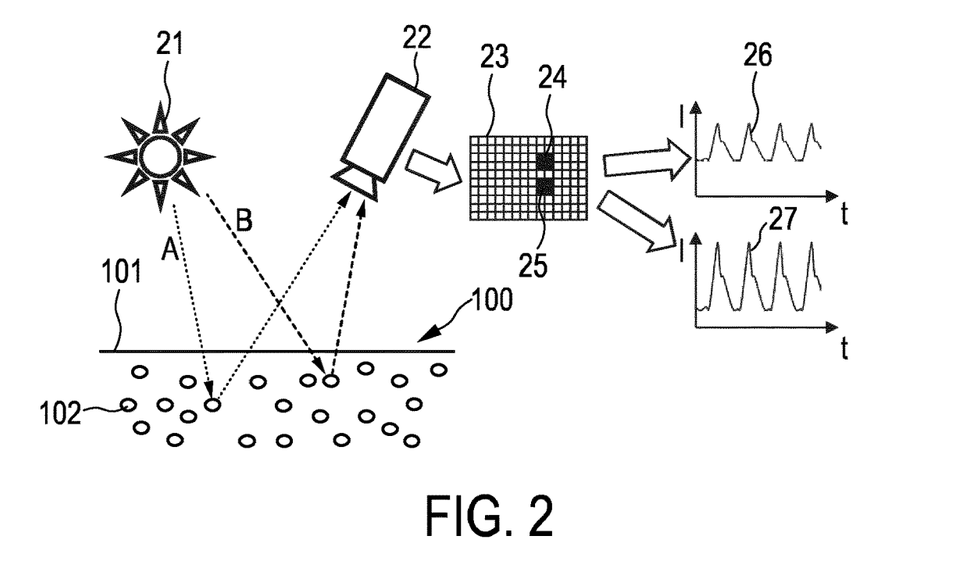
FIG. 2 illustrates the determination of vital sign information with the system according to the present invention.

FIG. 2 shows a (natural or artificial) light source 21, a detection unit 22 (e.g. an imaging unit like a camera) and a skin tissue 101 of a subject 100. The skin tissue 101 comprises blood vessels 102. The light source 21 emits light at various wavelengths, in particular over the typical spectrum of ambient light, including light at at least a first wavelength (e.g. red light, indicated with a dotted line A) and a second wavelength (e.g. infrared light, indicated with a dashed line B). The light rays A, B penetrate into the skin 104 of the subject 100. Some of the light is absorbed within the skin tissue 101, while some of the light is reflected or scattered in the tissue and reaches the detection unit 22. The absorption and/or reflection characteristic is time-variant and represents the time-variant perfusion of the skin tissue 101 with its blood vessels 102.

The detection unit 22 comprises receiving optics, for example a receiver lens, and an array 23 of photo detectors or pixels that form an image sensor. The detection unit is configured to separate between at least two wavelengths (colors), e.g. red and infrared light, which may e.g. be achieved by use of respective filter or by use of different photo detectors or pixels that can only detect light of a specific wavelength. For instance, as shown in FIG. 2, light of a first wavelength is imaged onto a first group or array of pixels 24. Correspondingly, light of a second wavelength is imaged onto a second group of pixels 25.

Since the absorption of light in the skin tissue 101 is time-variant, the light intensity incident on the image sensor of the detection unit 22 is also time-variant. The time-variant intensity on the area of pixels 24 is depicted by curve 26. The time-variant intensity incident on the group of pixels 25 is depicted by curve 27. The intensity modulation depicted by curves 26 is due to the time-variant reflection in the skin tissue 101 at the first wavelength. The intensity modulation depicted by curve 27 is due to the time-variant reflection in the skin tissue 101 at the second wavelength.

The pulse rate of the subject 100, as one example of a vital sign of the subject can be directly determined from the time-variant intensity in one of the curves 26 or 27. For determining the blood oxygen saturation by photoplethysmography at least two wavelengths are required, as exemplarily explained below.

Contact pulse oximeters typically transmit red (R) and infrared (IR) (or, more precisely, in some cases near infrared) light through a vascular tissue of the subject of interest. The respective light portions (R/IR) can be transmitted and detected in an alternating (fast-switching) manner. Given that the respective spectral portions are differently absorbed by oxygenated hemoglobin (HbO$_2$) and reduced hemoglobin (Hb), blood oxygen saturation eventually can be processed. An oxygen saturation estimation algorithm can make use of a ratio of the signals related to the red and the infrared portion. The blood oxygen saturation in general is hereby referred to as SO$_2$. Furthermore, the algorithm can consider a non-pulsatile signal component. Typically, the PPG signal comprises a DC component and a relatively small pulsatile AC component. Furthermore, SO$_2$ estimation generally involves an empirically derived calibration factor applied to the processed values. Typically, the calibration factor (or, calibration curve) is determined upon reference measurements involving invasive blood oxygen saturation measurements. A calibration factor is required since a PPG device basically detects a ratio of (spectral) signal portions which has to be transferred into a blood oxygen saturation value which typically involves a ratio of HbO$_2$ and Hb. For instance, but not intended to limit the present disclosure, blood oxygen saturation estimation can be based on the following general equation:

$$SO_2 = \frac{HbO_2}{HbO_2 + Hb}, \qquad (1)$$

whereas PPG devices merely mediately detect HbO$_2$ and Hb from the spectral response at at least two wavelengths.

Generally, the measured intensity curve 26, 27 as a characteristic signal is considered to contain a considerably constant (DC) portion and an alternating (AC) portion superimposing the DC portion. Applying signal processing measures, the AC portion can be extracted and, furthermore, compensated for disturbances. For instance, the AC portion of the characteristic signal can comprise a dominant frequency which can be highly indicative of the subject's 100 vascular activity, in particular the heart beat. Still, the characteristic signal, in particular the AC portion, can be indicative of further vital parameters. In this connection, the detection of arterial blood oxygen saturation is an important field of application. As indicated above, basically, arterial blood oxygen saturation-representative values can be computed taking into account the behavior of the AC portion of the characteristic signal at distinct spectral portions thereof. In other words, a degree of arterial blood oxygen saturation can be reflected in different radiation absorbance at blood vessels. Furthermore, one can make use of the fact that the difference in absorbance due to the grade of oxygenation also varies significantly across different spectral portions. Moreover, also the DC portion of the signal can be utilized for blood oxygen saturation detection. Typically, the DC component represents the overall light absorption of the tissue, venous blood, and non-pulsatile arterial blood. By contrast, the AC component may represent the pulsatile arterial blood's absorption. Consequently, the determination of arterial blood oxygen saturation ($SaO_2$) can be expressed as:

$$SaO_2 = C \cdot \frac{(AC/DC)_{red}}{(AC/DC)_{infrared}}, \quad (2)$$

where C is a calibration parameter. C may stand for a large variety of calibration parameters applicable to the AC/DC relationship and should therefore not be interpreted in the strict algebraic sense of equation (2). C may, for example, represent a fixed constant value, a set of fixed constants or an adjustable calibration parameter. By way of example, another exemplary $SaO_2$ derivation model can be expressed as:

$$SaO_2 = C_1 + C_2 \cdot \frac{(AC/DC)_{red}}{(AC/DC)_{infrared}}, \quad (3)$$

where $C_1$ and $C_2$ can be considered calibration parameters of a linear approximation. In an exemplary embodiment, the signal calibration parameter determination can be directed to adjust or adapt the parameter $C_1$. Still, in the alternative, $SaO_2$ derivation may also be based on value tables deposited in (or accessible by) the device 1. The value tables (or: data bases) may provide for a discrete representation of the relationship between detected PPG signals and the desired calibration parameter. Also in that case an adaptable calibration parameter may be applied to improve the accuracy of the vital parameter determination.

It should be understood that the equations (2) and (3) are primarily presented for illustrative purposes. They should not be construed as limiting the scope of the present disclosure. In practice, the skilled person may determine and establish further appropriate $SaO_2$ derivation models. Alternative wavelength combinations, for example green and red, can be used depending on the substance to be detected. While the measurement of $SaO_2$ has been described in detail, this is to be understood as an example for the general concept of measuring the concentration of a substance in blood and/or tissue. Hereinafter, reference will be made to SpO2 which shall be understood as generally meaning the blood oxygen saturation measured by use of the above explained principles of remote plethysmography.

In summary, any selected region of interest (ROI) of skin exposed to the imaging unit can be used to derive the pulse oximetry raw waveforms, typically a time trace of red and infrared light, also known as photo-plethysmographic waveforms or PPG signals. As explained above various vital signs such as SpO2, pulse rate (PR), a perfusion index (Perf) and signal quality indicator (QI) can be derived from these raw signals.

The signal quality indicator (QI) may be an indicator of the cleanliness of the PPG signals and essential for a reliable SpO2 determination. Examples of a signal quality indicator and a method of determining it, which may be applied here, are e.g. described in U.S. Pat. No. 6,725,074 B1. This document particularly discloses a method of determining a quantitative statement concerning the quality of a medical measurement signal in pulsoximetry including the steps of determining factors relevant to the measurement signal and interlinking the factors by means of an uncertain logic into a quality indicator. The factors relate to combinations selected from the group consisting of signal recording, signal processing, and signal evaluation. The uncertain logic includes fuzzy logic. The quality indicator quantitatively describes a quality of a determined measurement value of the measurement signal.

Therefore, any (multi-wavelength) pixel i or pixel group i of a video camera can be used frame-to-frame to create these plethysmographic waveforms and calculate the corresponding numerical results SpO2_i, PR_i, Perf_i, QI_i. At minimum the imaging unit must be capable to create two colors of the image, typically red and infrared image, in a well-controlled wavelength range for accurate measurements.

Any combination of corresponding pixels or pixel groups between the two of more colors can be used to create a plurality pulse oximetry raw signals and its derived numerical values SpO2_i, PR_i, Perf_i and QI_i.

For practical purposes of processing power and achieving acceptable signal-to-noise ratios it is beneficial to cluster adjacent pixels into multiple bins.

Figure 3:
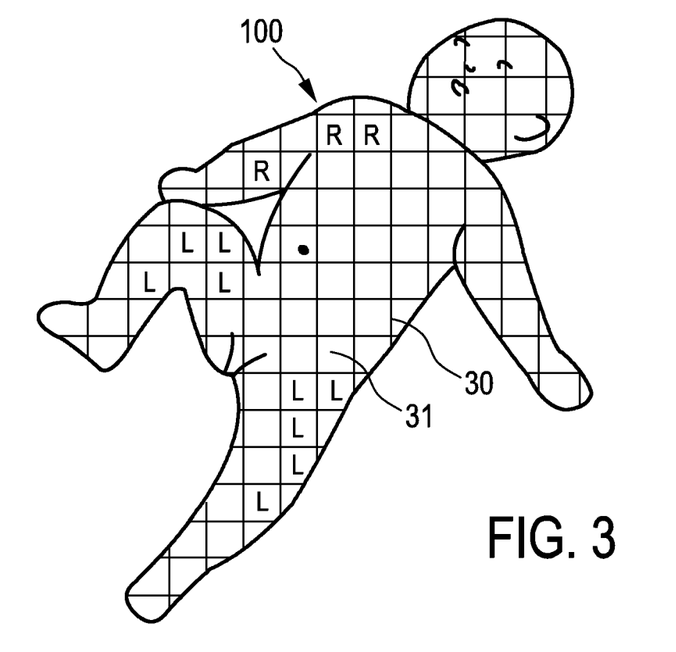
FIG. 3 shows a contour image of a baby lying on the back with the body area divided by a square grid pattern.

One method is to put a grid over the image containing the subject's body and sum the all the pixels within a grid area (also called tile) to create a pixel group i as shown in FIG. 3 illustrating a contour image of a baby 100 lying on the back with the body area divided by a square grid pattern 30 (or tile pattern; R indicating a tile of the right arm and L indicating a tile of a leg). It is understood that the grid 30 does not necessarily be square and the tiles 31 do not need to be square or have straight borders. A tile 31 is just a group of adjacent pixels of the image. The grid pattern 30 could also be formed following the body outline and divided by achieving a minimum pixel area.

Figure 4:
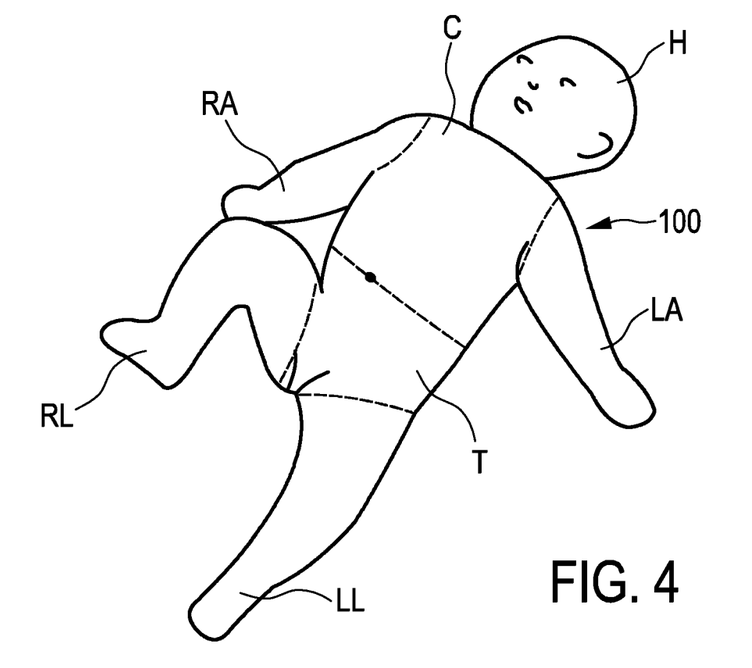
FIG. 4 shows a contour image of a baby illustrating the identification and separation into body parts.
Figure 5:
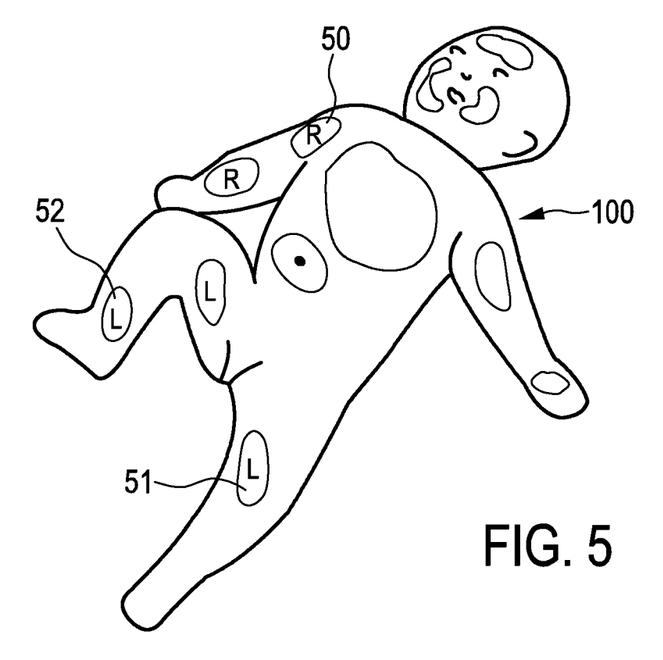
FIG. 5 shows a contour image of a baby illustrating the definition of ROIs by areas of acceptable perfusion index (AC/DC ratio)

Another method is to recognize certain body parts of the baby 100 first and define their contour and pixels belonging to the respective body part as shown in FIG. 4 illustrating the identification and separation of the contour image of the baby 100 into body parts. Body parts of interest in this context (in particular of CCHD screening) are left leg (LL), right leg (RL), left arm (LA), right arm (RA), head/face (H), chest (C) and trunk (T). The body parts may be further split into one or multiple ROIs (50 indicating an ROI of the right arm; 51, 52 indicating ROIs of a leg) as shown in FIG. 5 depending on minimum acceptance criteria. The different ROIs 50, 51, 52 can be processed independently or lumped together in total or for interesting body parts.

Figure 6:
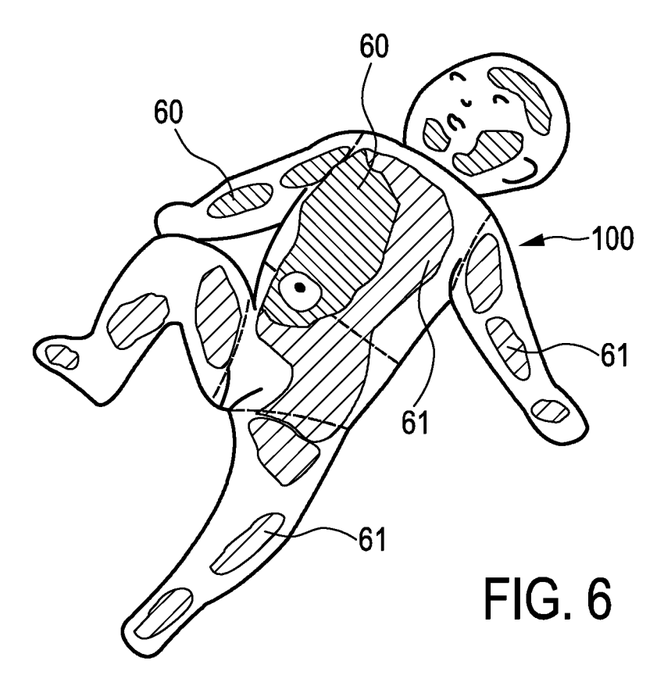
FIG. 6 shows a false color SpO2 map and qualified ROI on a cyanotic baby.

When going down to the pixel detail or small pixel groups a map of the body can be created associating SpO2_i, or PR_i or Perf_i to each pixel or pixel group. This map can be presented as false color image as shown in FIG. 6 for one or more (e.g. each) parameter. For SpO2 intuitive colors can be used like bright red (areas 60) for high oxygen saturation values and blue (areas 61) for low values. Similarly, false color images for pulse rate and perfusion index can be created.

For the purpose of screening a subject, such as a baby, for potential critical heart problems the baby will be laid on a mattress, preferably under a radiant warmer as shown in FIG. 1, as it needs to be basically naked maybe except some diapers. The screening is advantageously done at about 24 hours after birth were the baby is still not overly active and will not have lots of muscle strengths and move body parts.

It should be noted that FIGS. 3 to 6 show the baby 100 lying on the back (supine position). But it shall be understood that the baby 100 could also be in other positions for screening like on the side or on the belly (prone position) with the face turned to the side. The camera is assumed to be positioned more or less central vertical above the baby 100 as shown in FIG. 1.

The processing unit 3 of the proposed system is generally configured to carry out the steps of recognizing the subject within an image frame, locating body parts of interest of the subject including at least the right upper extremity (e.g. right arm) and at least one lower extremity of the subject, determining, per body part of interest, the perfusion index and the blood oxygen saturation level for a plurality of pixels and/or pixel groups of the subject from pulse oximetry waveforms for at least two different wavelengths contained in the image frames, wherein the determined perfusion index is used to select, per body part of interest, pixels and/or pixel groups, for which the previously determined blood oxygen saturation levels are binned per body part of interest or for which the pixel intensities are binned per body part of interest before determining the respective blood oxygen saturation level from the binned pixel intensities, determining a difference blood oxygen saturation level between the determined blood oxygen saturation level for the right upper extremity and the determined blood oxygen saturation level for the at least one lower extremity, and comparing the determined difference blood oxygen saturation level, the determined blood oxygen saturation level for the right upper extremity and the determined blood oxygen saturation level for the at least one lower extremity to respective blood oxygen saturation level thresholds to obtain a screening indicator for the subject indicating the quality of the subject's oxygenation.

Figure 7:
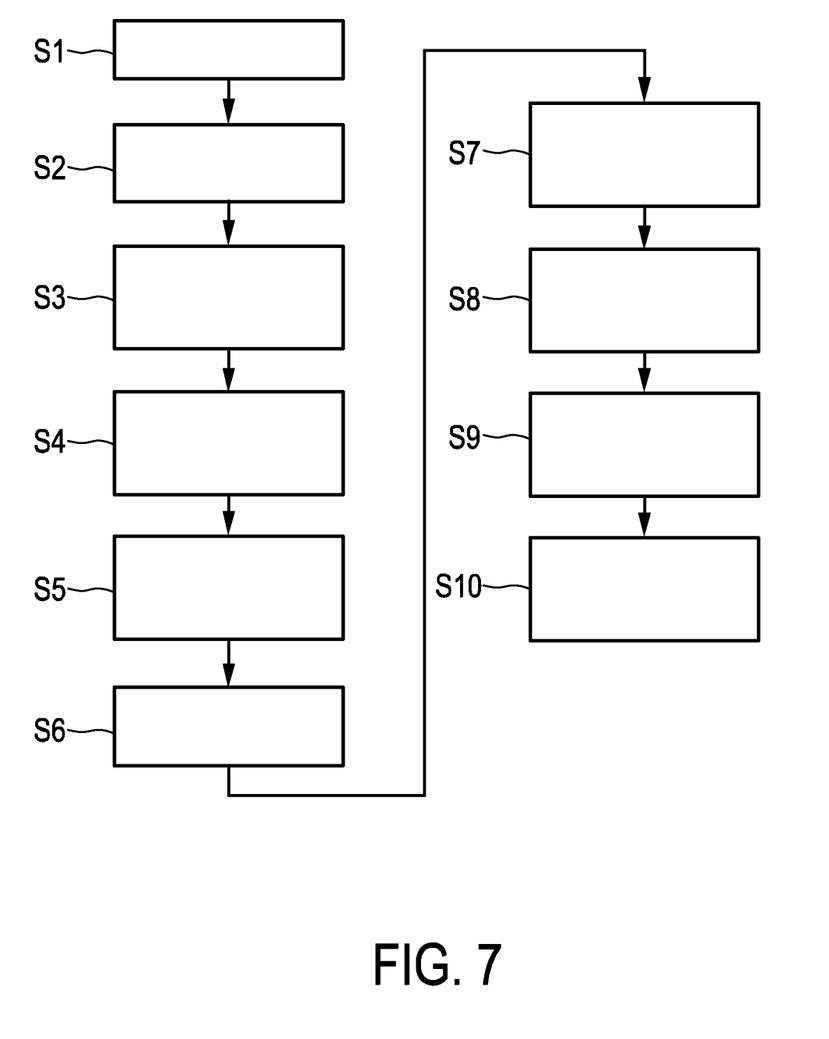
FIG. 7 shows a flowchart of a first preferred embodiment of the steps of the processing method as performed by the processing unit in order to perform a screening.

FIG. 7 shows a flowchart of a first preferred embodiment of the steps of the processing method as performed by the processing unit 3 in order to perform a screening. It is assumed that the camera 2 has been taking a continuous video stream at the required minimum frame rate for this purpose (e.g. 30 frames/sec) after pressing a start button. Several (or preferably all) image frames are then subjected to the steps illustrated in FIG. 7.

Step S1 consists of locating the baby 100 within the image frame by finding its outlines by commonly known methods in the art of object recognition (e.g. using a image segmentation or object recognition algorithm).

In step S2 a plurality (preferably each) pixels or binned groups of adjacent pixels are processed to derive pulse oximetry waveforms for at least two colors by tracking the intensity levels over time. With the well know algorithms for pulse oximetry (ratio-of-ratios, as explained above) a set of numerical results is computed for these groups. The set preferably comprises at least SpO2 and perfusion index (Perf), preferably also pulse rate (PR) and a signal quality indicator (QI). This step creates a set of values for the tiles covering the subject's body as shown in FIG. 3.

In step S3 the body parts of interest, including at least the right arm and one or two legs for CCHD screening practice, are located within the outline as determined in step S1.

In step S4 the pixel groups are checked, per body part of interest, for their perfusion (AC/DC) level (and, preferably and if available, the quality of the PPG signal) and subjects these to minimum acceptance criteria, e.g. AC/DC>that a threshold (e.g. 0.02%). Pixel groups that fail are dismissed from further processing.

In step S5 an image for display is created that e.g. shows a monochrome image of the baby, which favors the body contour and overlays false colors on the selected pixel groups with acceptable signal properties. An example of such an image is shown in FIG. 6.

In step S6 the accepted pixel groups of step S4 are grouped together for each body part of interest separately. The results for each pixel group of the same body part are averaged to make up one set of SpO2 and Perf (and preferably PR and QI) for each body part.

In step S7 it is indicate that the whole sequence from step S2 to step S6 is repeated from image frame to image frame for a period of time that is believed to be necessary to get a solid baseline of the current oxygenation status. A certain period in the order of minutes is generally required since the vital sign values are generally dynamic in time.

In step S8 the overall SpO2 result for "right arm" is compared with the overall SpO2 result of "leg(s)". Overall means that the average, median, difference and standard deviation (if more than two elements) of the binned areas for each of the two body parts are calculated and considered in presenting the results. It is understood that at the same time the other parameters from the pulse oximetry measurements (PR, Perf, QI) can considered in a similar fashion for qualifying the results (PR should be the same; QI should be good enough, e.g. above a set quality threshold) and for clinical interpretation (perfusion levels are e.g. of interest for the subject's cardio-vascular state).

In step S9 at least the three measures that are commonly used for assessing CCHD are displayed:

The SpO2_R of right arm (pre-duct);

The SpO2_L of one or both leg(s) (post-duct);

The difference SpO2_R−SpO2_L;

In step S10 indicators are applied to the three results by comparing them to thresholds that are predetermined or can be (pre-)defined by the user. Suggestions in clinical papers for instance are that SpO2 values should not be lower than 95% and the SpO2 difference should not be larger than 3% for healthy babies.

The presented system and method generally provide the flexibility to set the rules by the user. This also includes any logical combination of the above mentioned three tests applied in step S9 to create an overall CCHD indicator.

Such an indication could be done with some sort of flag associated with the results or a color field associated with the number. For instance, a color field could be colored in green if desired limits are exceeded on the acceptable side and in red if the limit is exceeded on the non-acceptable side. It is understood that there could also be an additional transitional range defined between red and green that is e.g. marked yellow. The yellow state would indicate that results are not really bad (red) or really good (green).

This final step gives an intuitive indication of the overall screening result, such as:
"Red": Not OK! Baby likely suffers from disease and needs further examination;
"Yellow": Repeat. Baby is "on the fringe"; screening should be repeated later;
"Green": OK! Baby can be considered healthy.

Figure 8:
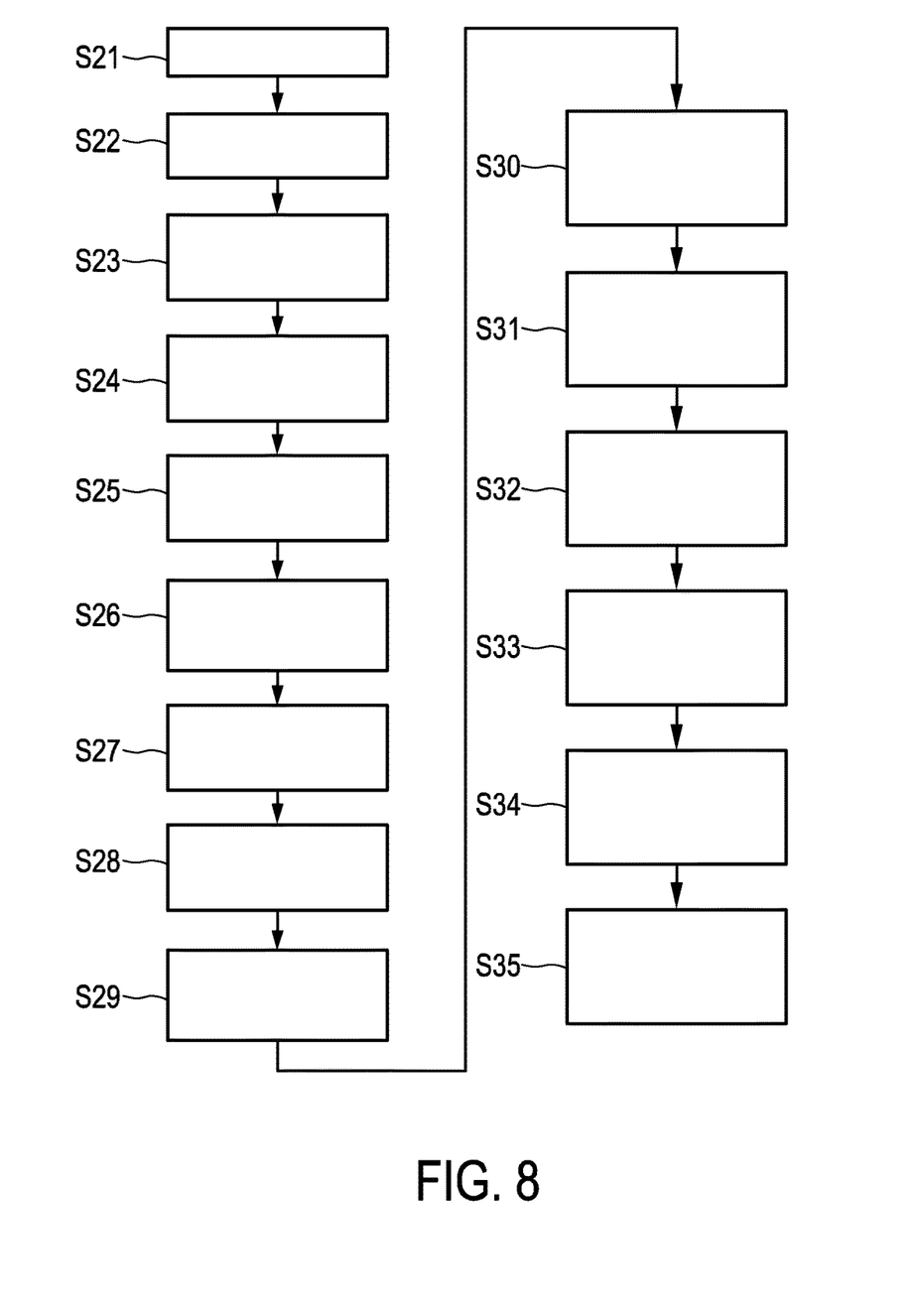
FIG. 8 shows a flowchart of a second preferred embodiment of the steps of the processing method as performed by the processing unit in order to perform a screening.

FIG. 8 shows a flowchart of a second preferred embodiment of the steps of the processing method as performed by the processing unit 3 in order to perform a screening.

Step S21 is identical to step S1 and consists of locating the baby 100 within the image frame by finding its outlines by commonly known methods in the art of object recognition.

In step S22 the body parts of interest, including at least the right arm and one or two legs for CCHD screening practice, are located within the outline as determined in step S21.

In step S23 "odd" areas are excluded from the region of interest. "Odd" areas include body surface areas that do not expose bare skin, e.g. diapers, hats, hair, eyes, tubes, sensors, labels. Such areas are e.g. identified again using commonly known methods for object recognition, e.g. using segmentation or pattern recognition. Thus, this step eliminates the pixels within the body outline that could cause problems in the following evaluation, e.g. saturated pixels due to bright reflections, "hot" or dead pixels due to technical reasons. In this context a hot pixel in a display is a pixel that is always on full power and cannot be controlled. A dead pixel is the same but always dark.

In step S24 the pixels, more precisely the intensity values of the pixels, that have not been excluded in step S23 are taken and binned into one intensity value (per color), i.e. they are added up. This results in one sample of the photo-plethysmographic raw wave (PPG signal). In case of a 3-color camera this results in 3 samples of the PPG signal.

In step S25 the perfusion (or pulsatility) index is computed for each sample of the PPG signal. This is the AC/DC ratio where AC is representing the modulation of reflectance due to the heart pulse activity. This gives an overall input to calculate an estimate of the whole body pulse oximetry values.

Step S26 now gets down into the smaller areas of the body. It divides the body outline as determined in step S21 into many smaller subareas. This could be done by some sort of grid of tiles as shown in FIG. 3 or other ways of dividing the body contour. Another method can be to form contour lines as on an altitude map and split the area between contour lines into small spots. Any method of clustering adjacent pixels will do.

In Step S27 such tiles are taken and the AC/DC, i.e. the perfusion or pulsatility index, is computed per tile, just as in step S25 it was done for the complete body.

In step S28 a minimum requirement is applied to the level of AC/DC. This step will exclude tiles that don't show enough pulse modulation and therefore become useless for pulse oximetry determinations. The step will exclude tiles that do not show exposed skin or skin areas with insufficient pulse modulation. This step makes use of the color channels available and considers AC and DC values, preferably all AC and DC values, for exclusion or inclusion. This step can include the results of step S25 as comparison to the overall perfusion level as well as the statistics of the tiles. Exclusion criteria beyond fix thresholds may include components like: dismiss the 20% of the tiles that have lowest AC/DC. This step leaves over a set of adjacent or non-adjacent tiles spread over the whole body outline.

In step S29 all tiles that belong to a certain body part as located per step S22 are binned. This leaves now pooled intensity values (per color) for each body part. Body parts of interest are for example shown in FIG. 4 and include at minimum the right arm (RA) and one or two legs (LR, RR) or the left arm (LA). Other body parts may be of clinical interest for CCHD screening or other disease symptoms in screening applications. For example, the cheek may be used representing a central part of blood supply. The whole head or part of it could be lumped together to create the oxygenation status of that body part.

In step S30 the pulse oximetry parameters is computed for the bins obtained in step S29, i.e. preferably for all the body parts.

In step S31 use is made of the results of step S30 together with steps S21 and S22 to display the numerical results in a graphical way as false colors on the body outline image. The result is similar to FIG. 6 if step S27 would not only calculate the perfusion of each tile but all parameters including SpO2. It should be noted that FIG. 6 does not show the tiles explicitly and suggests that they are very small. If the results of step S30 are taken instead the whole area associated with a body part can be colored with the one value as average for the body part.

In step S32 it is indicated that the whole procedure from step S23 to step S31 is repeated for several image frames in the video stream for a given period of time.

Steps S32 to S35 are substantially identical to steps S7 to S10 of the embodiment shown in FIG. 7.

The averaging process of tiles or sub areas for a body part for a single SpO2 is optimally done in a preferred embodiment as weighted average with the corresponding perfusion index or QI serving as weighing factor. This promotes the "better" areas to give a more reliable result.

A preferred indicator for CCHD is the difference post-duct to pre-duct. In a more general manner the SpO2 difference of the tiles or smaller body areas can be presented in false colors with respect to the overall SpO2 average as a kind of SpO2 gradient map. This promotes visibility of small differences as compared to presenting the complete range of SpO2.

Camera SpO2 could suffer from calibration offsets leading to less accurate readings. This issue is addressed in an embodiment by adding at least one normal pulse oximetry channel and probe to the baby and calibrating the corresponding camera reading of this extremity to that value as a kind of in vivo one-point calibration. I.e. an offset SpO2 is added to the camera reading for the extremity to match the pulse oximeter SpO2 numbers:

Offset=SpO2_cam_LL−SpO2_pulseox_LL.

This offset can then be applied to all the individual camera SpO2 readings for sub areas i:

SpO2_cam_$i$_corrected=SpO2_cam_$i$−Offset.

Figure 9:
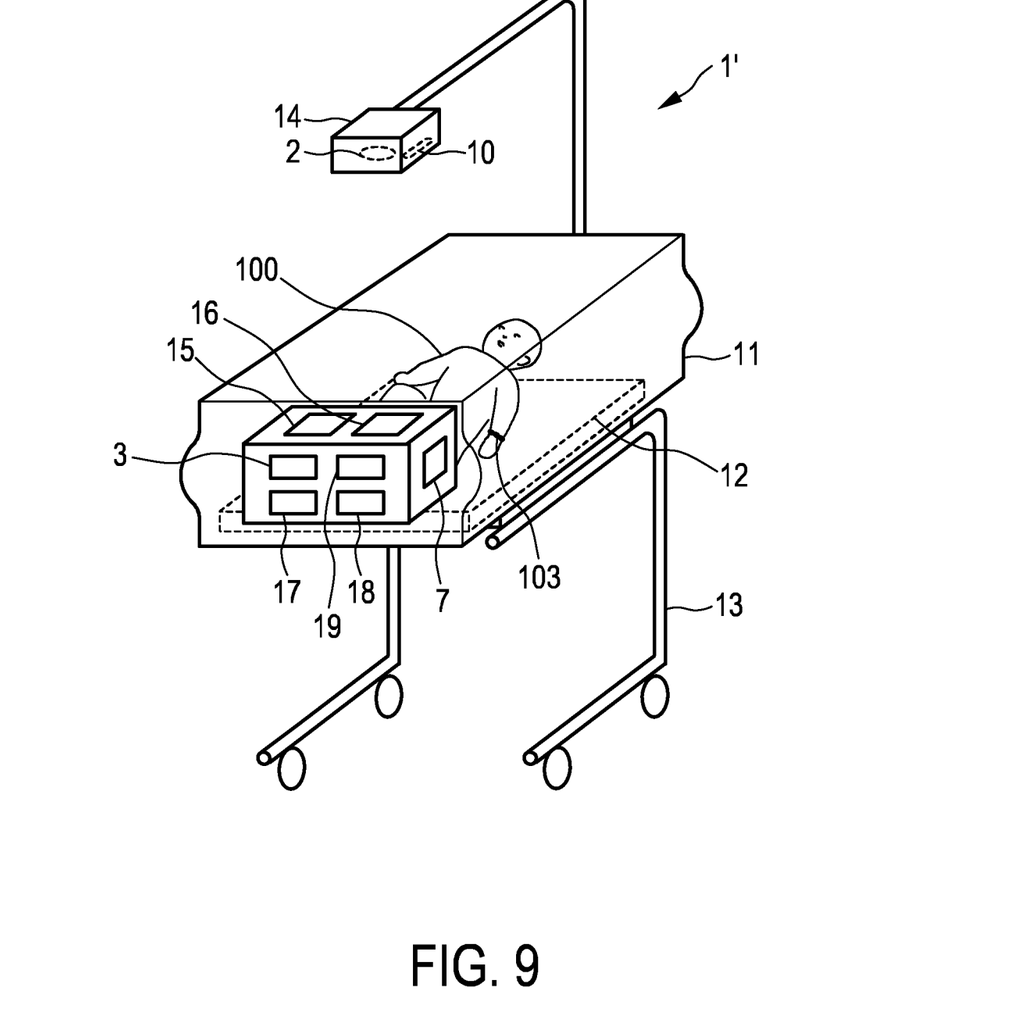
FIG. 9 shows another exemplary embodiment of the system for screening of oxygenation of a subject according to the present invention.

FIG. 9 shows another embodiment of a system 1' according to the present invention. It comprises a bassinette 11 containing a mattress 12 and being mounted on a roll stand 13 having wheels to provide mobility to the system F. The bassinette 11 is arranged at a central place to hold the baby 100 and other system components. In particular, it comprises a camera unit 14 comprising the imaging unit (camera) 2 and a light source 10 to provide a good central spot to image the baby's body well. A display 15 and a control unit 16 are positioned at a convenient place for the operator to operate the system and see the results. That part may also contain the other elements of the system like the processing unit 3, a printer 17 to document the screening results, a storage 18 to log baby's screening results and an interface 19 to provide connectivity to a hospital information system (HIS), e.g. to enable downloading screening results to the hospital information system.

Generally, it is sufficient if the scenery is illuminated by ambient light, i.e. sunlight and/or light from an artificial light source, which directly or indirectly emit light towards the subject 100. In addition, or in the alternative, the system 1 can also comprise a light source that emits and directs light towards the subject 100. The use of a light source is particularly beneficial if the ambient light sources do not provide sufficient light or if the spectrum of the ambient light sources does not provide sufficient power at the desired wavelengths. In order to provide the best possible signal to the camera 2 and to obtain a good signal-to-noise ratio it preferred to use such a dedicated illumination. The optimal setup for best screening results would ensure little shadowing impact by operator, adequate light levels for each color channel, and relatively well-defined camera/light position with respect to the subject 100.

The optional control unit 16 is configured to particularly control the sensitivity of the imaging unit 2 and/or to control the power of the light source 10. Because the dynamic range of a detector or image sensor that is used as imaging unit 2 is limited, shutters and electronic offsets may have to be adjusted according to the lighting situation in the observed scene. The light source 10 can be part of a control loop which sets an optimal operating point of the image sensor of the imaging unit 2. Optimal in this context refers to an output signal without signal clipping, no saturation of individual detectors of the image sensors and a good signal-to-noise ratio at least for the detector area corresponding to first and/or second marker area.

Newborn babies generally carry a tag 103 in form of a wrist band for identification purposes. The tag 103 may be designed is such a way that the camera 2 used could be shared at the same time to recognize the patient ID tag 103 and automatically assign the screening results to this baby 100 in the screening records. An extra identification unit 7, such as a particular processor or software running on the processing unit 3, may be provided for identifying the baby 100 from one or more image frames. Know methods of electronic identification by imaging systems and cameras as e.g. used in bar code scanners or optical character recognition systems as found along with image scanners can be used for this purpose. This approach gives a high measure of security in matching screening results to a patient record. It yields lower cost than a system with separate automatic recognition system like a RFID receiver or dedicated bar code scanner.

Figure 10:
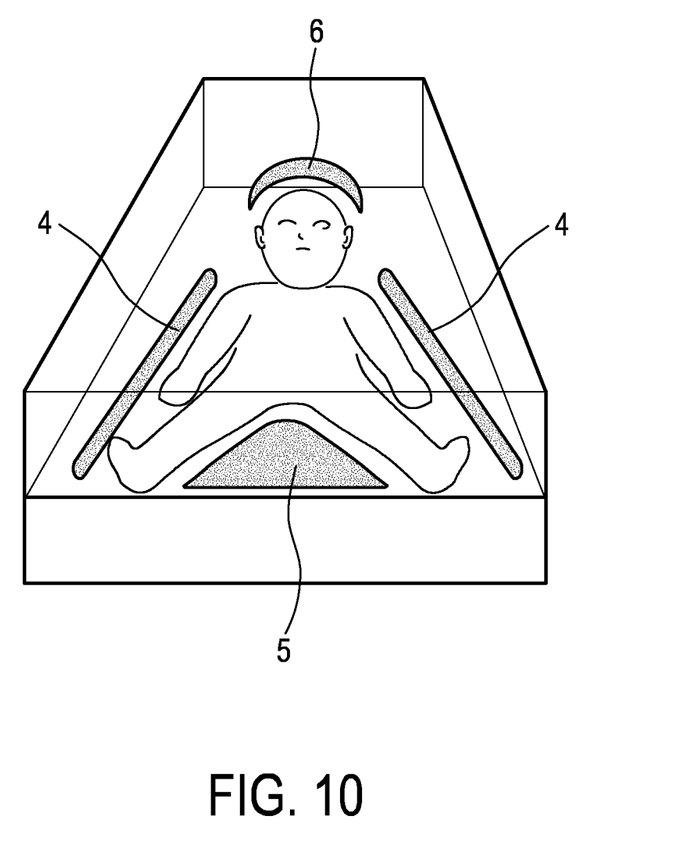
FIG. 10 shows an embodiment of holding elements for holding the subject in place during a screening procedure.

FIG. 10 depicts an example how special holding elements 4, 5, 6 (also called fixation means) could be applied to minimize movement artifacts during the measurement. In this example the baby 100 is surrounded by several barrier parts that can be adapted to the baby's shape and size. The elements 4 can be moved in from the side wall to keep the arms to the trunks and down. The element 5 can be used together with elements 4 to fix the legs of the baby. The element 6 can be moved down from the top wall to hold the baby's head upright. The barrier materials could be part of the mattress system and be held on the mattress cover, e.g. by Velcro fastener or any other fixation. It could also be part of the bassinette construction and slide in and out for fixation.

It is understood that the design must put little pressure on the baby not to constrict skin perfusion as well as it should not block camera view much. The barriers could also contain optical elements (e.g. LEDs and photodiodes) to constitute a regular SpO2 probe. If receiver and transmitter are side by side they could form a reflectance probe. If the barrier contains a sort of loop it could also constitute a transmission probe that partially of fully wraps around an arm or leg.

By way of example, the present invention can be applied in the field of health care, in particular for unobtrusive remote monitoring or screening of patients or newborn babies. Various vital signs can generally be monitored and used for screening. Particularly for screening of newborn babies for CCHD (and potentially other heart anomalies) the invention is very useful.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for screening of a state of oxygenation of a subject, said system comprising an imaging unit for obtaining a plurality of image frames of the subject over time, said system further comprising a processor configured to process the image frames by:
   recognizing the subject within an image frame,
   locating body parts of interest of the subject including at least a right upper extremity and at least one lower extremity of the subject,
   determining, per body part of interest, the perfusion index,
   selecting, per body part of interest, a plurality of pixels and/or pixel groups by use of said perfusion index,
   determining the blood oxygen saturation level for said plurality of pixels and/or pixel groups of the subject from pulse oximetry waveforms for at least two different wavelengths contained in the image frames,
   determining a difference blood oxygen saturation level between the determined blood oxygen saturation level for the right upper extremity and the determined blood oxygen saturation level for the at least one lower extremity, and
   comparing the determined difference blood oxygen saturation level, the determined blood oxygen saturation level for the right upper extremity and the determined blood oxygen saturation level for the at least one lower extremity to respective blood oxygen saturation level thresholds to obtain an screening indicator for the subject indicating the quality of the subject's oxygenation.

2. The system as claimed in claim 1, wherein the processor is configured to:
   determine, separately for the right upper extremity and at least one lower extremity, a combined blood oxygen saturation level from the blood oxygen saturation levels obtained for different groups of image frames for different time sequences of image frames,
   determine the difference blood oxygen saturation level between the determined combined blood oxygen saturation level for the right upper extremity and the determined combined blood oxygen saturation level for the at least one lower extremity, and
   compare the determined difference blood oxygen saturation level, the determined combined blood oxygen saturation level for the right upper extremity and the determined combined blood oxygen saturation level for the at least one lower extremity to respective blood oxygen saturation level thresholds to obtain the screening indicator for the subject.

3. The system claimed in claim 1, wherein the processor is configured to determine a combined blood oxygen saturation level from the blood oxygen saturation levels obtained for different groups of image frames by forming an average, a median, a difference or a standard deviation.

4. The system as claimed in claim 1, wherein the processor is configured to determine, per body part of interest, the pulse rate and/or a quality index indicating the pulse oximetry signal quality and to use the determined the pulse rate and/or a quality index to qualify the obtained screening indicator.

5. The system as claimed in claim 1, wherein the processor is configured to use the determined perfusion index for selecting, per body part of interest, pixels and/or pixel groups, for which the previously determined blood oxygen saturation levels are binned per body part of interest, having a perfusion index above a perfusion threshold.

6. The system as claimed in claim 1, wherein the processor is configured to use the determined perfusion index for selecting, per body part of interest, pixels and/or pixel groups, for which the pixel intensities are binned per body part of interest before determining the respective blood oxygen saturation level from the binned pixel intensities, having a perfusion index above a perfusion threshold or fulfilling another selection criterion related to the perfusion index.

7. The system claimed in claim 1, wherein the processor is configured to:
   perform the following steps multiple times for different groups of image frames:
      recognizing the subject within an image frame,
      determining blood oxygen saturation level, pulse rate and perfusion index for a plurality of pixels and/or pixel groups of the subject from pulse oximetry waveforms for at least two different wavelengths, said pulse oximetry waveforms being obtained from said plurality of image frames,
      locating body parts of interest of the subject including at least the right upper extremity and at least one lower extremity of the subject,
      selecting, per body part of interest, pixels and/or pixel groups having a perfusion index above a predetermined perfusion threshold,
      displaying an oxygenation image of the subject in which for selected pixels and/or pixel groups the respective blood oxygen saturation level is displayed,
      binning, per body part of interest, the determined blood oxygen saturation level, pulse rate and perfusion index for the selected pixels and/or pixel groups,
   determining, separately for the right upper extremity and at least one lower extremity, a combined blood oxygen saturation level from the binned blood oxygen saturation levels obtained for the different groups of image frames,
   determining a difference blood oxygen saturation level between the determined combined blood oxygen saturation level for the right upper extremity and the determined combined blood oxygen saturation level for the at least one lower extremity, and
   comparing the determined difference blood oxygen saturation level, the determined combined blood oxygen saturation level for the right upper extremity and the determined combined blood oxygen saturation level for the at least one lower extremity to respective blood oxygen saturation level thresholds to obtain an screening indicator for the subject.

8. The system as claimed in claim 1, wherein the processor is configured to
   performing the following steps multiple times for different groups of image frames:
      recognizing the subject within an image frame,
      locating body parts of interest of the subject including at least the right upper extremity and at least one lower extremity of the subject,
      binning pixels of skin areas of the subject for at least two different wavelengths into a pulse oximetry waveform sample per wavelength,
      determining a whole skin area perfusion index from said pulse oximetry waveform samples,
      subdividing the image of the subject into subareas,
      determining a subarea perfusion index per subarea from said pulse oximetry waveform samples,
      selecting subareas having a subarea perfusion index fulfilling a subarea selection criterion,
      binning, per body part of interest, pixels of selected subareas,
      determining, per body part of interest, blood oxygen saturation level, pulse rate and perfusion index for said binned pixels for a body part of interest from pulse oximetry waveforms for said at least two different wavelengths, said pulse oximetry waveforms being obtained from said plurality of image frames,
      displaying an oxygenation image of the subject in which for the body parts of interest the respective blood oxygen saturation level is displayed, and
   determining, separately for the right upper extremity and at least one lower extremity, a combined blood oxygen saturation level from the binned blood oxygen saturation levels obtained for the different groups of image frames and,
   determining a difference blood oxygen saturation level between the determined combined blood oxygen saturation level for the right upper extremity and the determined combined blood oxygen saturation level for the at least one lower extremity, and
   comparing the determined difference blood oxygen saturation level, the determined combined blood oxygen saturation level for the right upper extremity and the determined combined blood oxygen saturation level for the at least one lower extremity to respective blood oxygen saturation level thresholds to obtain an screening indicator for the subject.

9. The system as claimed in claim 1, wherein the processor is configured to use the determined perfusion index to select, per body part of interest, said pixels and/or pixel groups, for which the previously determined blood oxygen saturation levels are binned per body part of interest or for which the pixel intensities are binned per body part of interest before determining the respective blood oxygen saturation level from the binned pixel intensities.

10. The system as claimed in claim 1, wherein the perfusion index represents an AC/DC ratio computed for a sample of a photoplethysmography (PPG) signal derived from the image frames where AC denotes the AC component of the PPG signal and DC denotes the DC component of the PPG signal.

11. The system as claimed in claim 9, further comprising a display for displaying an oxygenation image of the subject in which for selected pixels and/or pixel groups the respective blood oxygen saturation level is displayed.

12. The system as claimed in claim 11, wherein the display is configured to display the oxygenation image of the subject as a false color image in which for selected pixels and/or pixel groups the respective blood oxygen saturation level is displayed in false colors.

13. The system as claimed in claim 9, further comprising holding elements for holding the subject in place while the image frames are obtained and/or an identification unit for identifying the subject from one or more image frames by use of image recognition of an identification element worn by the subject.

14. A processing method for processing image frames obtained from a subject over time comprising the steps of:

recognizing the subject within an image frame, locating body parts of interest of the subject including at least a right upper extremity and at least one lower extremity of the subject, determining, per body part of interest, the perfusion index, selecting, per body part of interest, a plurality of pixels and/or pixel groups by use of said perfusion index, determining the blood oxygen saturation level for said plurality of pixels and/or pixel groups of the subject from pulse oximetry waveforms for at least two different wavelengths contained in the image frames, determining a difference blood oxygen saturation level between the determined blood oxygen saturation level for the right upper extremity and the determined blood oxygen saturation level for the at least one lower extremity, and comparing the determined difference blood oxygen saturation level, the determined blood oxygen saturation level for the right upper extremity and the determined blood oxygen saturation level for the at least one lower extremity to respective blood oxygen saturation level thresholds to obtain an screening indicator for the subject indicating the quality of the subject's oxygenation.

15. A device comprising:

at least one processor;

and at least one memory including computer executable program code;

the at least one memory and the computer program code configured to, with the at least one processor, cause the device at least to:

carry out the steps of the method as claimed in claim 14.

* * * * *